(12) United States Patent
McPhee

(10) Patent No.: US 11,911,076 B2
(45) Date of Patent: Feb. 27, 2024

(54) PEDICLE SCREWS

(71) Applicant: SOUTHERN CROSS PATENTS PTY LTD, Corinda (AU)

(72) Inventor: Robert McPhee, Corinda (AU)

(73) Assignee: SOUTHERN CROSS PATENTS PTY LTD, Corinda (AU)

( * ) Notice: Subject to any disclaimer, the term of this patent is extended or adjusted under 35 U.S.C. 154(b) by 0 days.

(21) Appl. No.: 17/293,718

(22) PCT Filed: Nov. 15, 2019

(86) PCT No.: PCT/AU2019/051260
§ 371 (c)(1),
(2) Date: May 13, 2021

(87) PCT Pub. No.: WO2020/097691
PCT Pub. Date: May 22, 2020

(65) Prior Publication Data
US 2022/0008103 A1 Jan. 13, 2022

(30) Foreign Application Priority Data
Nov. 16, 2018 (AU) .............................. 2018904378

(51) Int. Cl.
*A61B 17/70* (2006.01)
*A61B 17/86* (2006.01)

(52) U.S. Cl.
CPC ...... *A61B 17/7037* (2013.01); *A61B 17/7032* (2013.01); *A61B 17/8605* (2013.01)

(58) Field of Classification Search
CPC .................. A61B 17/70; A61B 17/7032–7046
See application file for complete search history.

(56) References Cited

U.S. PATENT DOCUMENTS

| 2006/0200131 A1* | 9/2006 | Chao | A61B 17/7037 |
| | | | 606/328 |
| 2007/0088357 A1* | 4/2007 | Johnson | A61B 17/7037 |
| | | | 606/86 A |
| 2008/0215100 A1* | 9/2008 | Matthis | A61B 17/7032 |
| | | | 606/301 |

(Continued)

FOREIGN PATENT DOCUMENTS

| EP | 1774919 A1 | 4/2007 | |
| EP | 1857064 A1 | 11/2007 | |
| GB | 2483531 A * | 3/2012 | ......... A61B 17/7037 |

OTHER PUBLICATIONS

International Search Report issued in Application No. PCT/AT2019/051260 dated Feb. 17, 2020.

(Continued)

*Primary Examiner* — Eduardo C Robert
*Assistant Examiner* — Michelle C Eckman
(74) *Attorney, Agent, or Firm* — Workman Nydegger

(57) ABSTRACT

A modular pedicle screw assembly for immobilisation and stabilisation of spinal segments in a patient. One example of the modular pedicle screw assembly includes a bone screw, a uniaxial inner collet arranged to cooperate with a head of the bone screw, a seat arranged to provide seating for retention of the inner collet, and an inner collet actuator designed to engage the seat to activate the inner collet for clamping about the head of the bone screw.

12 Claims, 13 Drawing Sheets

(56) References Cited

U.S. PATENT DOCUMENTS

| | | | |
|---|---|---|---|
| 2008/0262556 A1* | 10/2008 | Jacofsky | A61B 17/7032 606/301 |
| 2009/0062866 A1* | 3/2009 | Jackson | A61B 17/86 606/301 |
| 2010/0234902 A1* | 9/2010 | Biedermann | A61B 17/7037 606/305 |
| 2010/0305621 A1* | 12/2010 | Wang | A61B 17/7037 606/305 |
| 2011/0152949 A1* | 6/2011 | Biedermann | A61B 17/7037 606/305 |
| 2012/0143266 A1* | 6/2012 | Jackson | A61B 17/7032 606/328 |
| 2014/0046374 A1 | 2/2014 | Asaad et al. | |
| 2014/0121703 A1 | 5/2014 | Jackson et al. | |
| 2014/0188172 A1 | 7/2014 | Nichols et al. | |
| 2014/0277153 A1 | 9/2014 | Spratt et al. | |
| 2014/0343617 A1* | 11/2014 | Hannen | A61B 17/8605 606/306 |
| 2018/0021068 A1 | 1/2018 | May et al. | |

OTHER PUBLICATIONS

Written Opinion of the ISA issued in Application No. PCT/AT2019/051260 dated Feb. 17, 2020.
Extended European Search Report received for EP Patent Application No. 19884980, dated Jan. 7, 2022, 9 pages.
International Preliminary Reporton Patentability received for PCT Patent Application No. PCT/AU2019/051260, dated Mar. 5, 2021, 33 pages.
India Office Action, dated Nov. 22, 2022, from Indian Patent App. No. 202117025826.

* cited by examiner

PEDICLE SCREWS

The present application is a U.S. National Stage of International Application No. PCT/AU2019/051260, filed on Nov. 15, 2019, designating the United States and claiming the priority of Australian Patent Application No. 2018904378 filed with the Australian Patent Office on Nov. 16, 2018. All of the aforementioned applications are incorporated herein in their respective entireties by this reference.

TECHNICAL FIELD

The present invention is broadly directed to a modular pedicle screw assembly or sub-assembly configurable for either uniaxial movement in the sagittal and transverse planes, or polyaxial movement. The invention also relates broadly to a uniaxial pedicle screw assembly and relates particularly, although not exclusively, to a uniaxial pedicle screw sub-assembly.

BACKGROUND OF INVENTION

In the field of spinal fixations there are a plethora of pedicle screw systems available. The screw systems are typically designed for polyaxial, monoaxial, or uniaxial movement lending themselves to certain spinal indications. For example, sagittal uniaxial screws are generally used in a coronal imbalance of the spine whereas a transverse uniaxial screw is used in a sagittal imbalance of the spine. In order to restore, immobilize and stabilize acute and chronic instabilities or deformities of the spine, a spinal surgeon must carry a large amount of stock of pedicle screw options in order to treat the various spinal pathologies. This adds inventory mass into the surgical field and increases the cost of sterilisation, shipping and inventory stock holdings.

The patent literature is replete with pedicle screw systems associated with spinal fixations. Some of these patents are directed to screw systems where an anchor is configured to cooperate with the head of a bone screw to limit movement of the anchor and an associated rod. US patent application publication nos. 2017/0049484 and 2015/0134004 are examples of pedicle screw assemblies of this nature where the rod is locked within the anchor. These assemblies are relatively complicated in construction including an adaptor designed to lock movement of the anchor and the associated rod about the head of the bone screw. Other of prior patents are directed to polyaxial screw systems intended to provide universal movement to capture and anchor a rod. U.S. Pat. No. 7,186,255 discloses one example of a polyaxial screw assembly of this type including a collar which assists in locking of an associated swivel to the bone screw effectively reducing it to a monoaxial screw.

SUMMARY OF INVENTION

According to a first aspect of the present invention there is provided a uniaxial pedicle screw sub-assembly comprising:

a bone screw having a threaded bone shaft adapted for insertion in a vertebra;

a uniaxial inner collet configured in an operative position to clamp about a head of the bone screw, said head being substantially ball-shaped with a truncated surface arranged to cooperate with a corresponding bearing surface of the inner collet in an inoperative position to permit tilting of the inner collet about a tilt axis of the head of the bone screw;

a seat arranged to provide seating for retention of the inner collet, the seat designed to tilt in conjunction with the inner collet in the inoperative position about the tilt axis of the head of said bone screw.

According to a second aspect of the invention there is provided a uniaxial pedicle screw assembly comprising:

a bone screw having a threaded bone shaft adapted for insertion in a vertebra;

a uniaxial inner collet configured in an operative position to clamp about a head of the bone screw, said head being substantially ball-shaped with a truncated surface arranged to cooperate with a corresponding bearing surface of the inner collet in an inoperative position to permit tilting of the inner collet about a tilt axis of the head of the bone screw;

a seat arranged to provide seating for retention of the inner collet, the seat designed to tilt in conjunction with the inner collet in the inoperative position about the tilt axis of the head of said bone screw;

an inner collet actuator designed to engage the seat to activate the inner collet for movement into the operative position for clamping about the head of the bone screw to lock the inner collet and the seat to the head of said bone screw.

Preferably the uniaxial pedicle screw sub-assembly and assembly is of a modular construction.

According to a third aspect of the invention there is provided a modular pedicle screw assembly comprising:

a bone screw having a threaded bone shaft adapted for insertion in a vertebra;

an inner collet selected from either a uniaxial inner collet or a polyaxial inner collet each configured in an operative position to clamp about a head of the bone screw, said head being substantially ball-shaped with a truncated surface wherein:

i) the uniaxial inner collet includes a bearing surface corresponding to the truncated surface of the head of the bone screw, said bearing surface being arranged to permit tilting of the inner collet in an inoperative position about a tilt axis of the head of said bone screw;

ii) the polyaxial inner collet includes a cavity defining an internal surface configured to permit polyaxial movement of the inner collet in the inoperative position about the head of said bone screw;

a seat arranged to provide seating for retention of the inner collet, the seat designed to move either uniaxially or polyaxially in conjunction with the selected inner collet in the inoperative position about the head of said bone screw;

an inner collet actuator designed to engage the seat to activate the selected inner collet for movement into the operative position for clamping about the head of the bone screw to lock the selected inner collet and the seat to the head of said bone screw.

Preferably the uniaxial inner collet includes a plurality of claw elements together configured in the inoperative position of the inner collet to permit tilting of the inner collet about the tilt axis of the head of the bone screw. More preferably at least one of the claw elements includes a bearing surface defining the corresponding bearing surface of the uniaxial inner collet configured to cooperate with the truncated surface of the head of the bone screw to permit tilting of the uniaxial inner collet in the inoperative position about the fixed tilt axis of the head of said bone screw. Even more preferably the bearing surface of the claw element is one of a pair of opposing bearing surfaces formed in respective of an opposing pair of the plurality of claw elements, the pair of opposing bearing surfaces arranged to cooperate with respective of a pair of the truncated surfaces in the head of the bone screw.

Preferably the seat includes a recess within which the inner collet seats for retention in either the inoperative or operative positions, the inner collet being movable via the inner collet actuator from i) the inoperative position where the head of the bone screw is received within the inner collet with radial separation of the claw elements of the inner collet into the recess of the seat, to ii) the operative position where the head of the bone screw is clamped within the inner collet with clamping of the claw elements about the head of the bone screw. More preferably the seat includes an aperture formed continuous with the recess and arranged for receipt of the head of the bone screw into the inner collet which is retained in the inoperative position for seating in the recess of the seat. Even more preferably the recess of the seat includes an annular rebate configured, with the inner collet in the inoperative position, to permit the radial separation of the claw elements of the inner collet into the annular rebate on receipt of the head of the bone screw into the inner collet. Still more preferably the seat includes an annular flange defining the aperture through which the head of the bone screw is received, said flange configured with the inner collet in the operative position to urge the claw elements of the inner collet for clamping about the head of the bone screw.

Preferably the pedicle screw assembly also comprises a rod for securement to the seat. More preferably said assembly further comprises a locking element operatively coupled to the seat to lock the rod to the seat. Even more preferably the inner collet actuator serves as the locking element wherein the inner collet actuator is in the form of a set screw arranged to engage the seat for activation of the inner collet and to lock the rod to the seat. Alternatively, the inner collet actuator is independent of the locking element wherein the inner collet actuator is in the form of an external set screw arranged to engage the seat for activation of the inner collet, and the locking element is in the form of an internal set screw arranged to engage the external set screw for locking of the rod to the seat.

Preferably the seat also includes a pair of legs defining a pair of opposing and axially oriented channels arranged for receipt of the rod for locking to the seat via the locking element. More preferably the inner collet includes a pair of radially extending arms aligned with one another and arranged for seating within the pair of opposing channels of the seat thereby orienting the rod at a fixed angular disposition relative to the tilt axis of the head of the bone screw, said angular disposition determined by the angular position of the bearing surface of the uniaxial inner collet relative to the pair of radially extending arms. In one embodiment, said arms are directionally parallel with the bearing surface of the uniaxial inner collet wherein the rod is oriented substantially perpendicular with the tilt axis of the head of the bone screw about which the inner collet in the operative position is arranged to tilt. In an alternative embodiment, the pair of arms of the uniaxial inner collet are directionally perpendicular with the bearing surface of said inner collet wherein the rod is oriented substantially parallel with the tilt axis of the head of the bone screw.

Preferably the inner collet also includes a pair of legs disposed either side of the pair of radially extending arms, said legs of the inner collet defining a pair of opposing and axially oriented channels substantially aligned with the channels of the seat and arranged for receipt of the rod. More preferably each of the legs of the inner collet include a protrusion designed for releasable retention within a corresponding opening in the legs of the seat to retain the inner collet within the seat in both the inoperative and operative positions.

Preferably the modular pedicle screw assembly also comprises an insert frangibly connected to the polyaxial inner collet to release from said inner collet and locate at the truncated surface of the head of the bone screw, the polyaxial inner collet in i) the inoperative position thus being mobilised for polyaxial movement about the head of the bone screw, and ii) in the operative position arranged for clamping about the head of the bone screw having its effective clamping surface increased by the insert located at the truncated surface of said screw head. More preferably the insert is one of a pair of inserts frangibly connected to respective of a pair of opposing claw elements of the polyaxial inner collet, said pair of inserts configured in the operative position of the polyaxial inner collet to locate at respective of the pair of opposing truncated surfaces of the head of the bone screw.

Preferably the set screw of the inner collet actuator threadably engages the legs of the seat for contact with the inner collet to effect its movement in a sliding action from the inoperative position to the operative position where the annular flange of the seat contacts the claw elements of the inner collet for clamping about the head of the bone screw with increasing pressure. More preferably the radially extending arms of the inner collet are arranged to rest at a base of the respective channels of the seat within which they are seated when in the operative position the inner collet is clamped about the head of the bone screw with sufficient locking pressure. Even more preferably the protrusion of each of the legs of the inner collet is retained for sliding movement within the corresponding opening of the legs of the seat during movement of the inner collet between the inoperative and operative positions.

Preferably the set screw of the inner collet actuator during movement of the inner collet from its inoperative to operative positions also effects locking of the rod to the seat. Alternatively the external set screw includes a threaded aperture within which the internal set screw is received for independent locking of the rod to the seat.

BRIEF DESCRIPTION OF DRAWINGS

In order to achieve a better understanding of the nature of the present invention a preferred embodiment of a modular pedicle screw assembly will now be described, by way of example only, with reference to the accompanying drawings in which.

DETAILED DESCRIPTION

As best seen in FIGS. 1 to 4, there is a modular pedicle screw assembly 10 for immobilisation and stabilisation of spinal segments in a patient (not shown). The pedicle screw assembly 10 is in the form of a surgical implant configured for the treatment of acute and chronic instabilities or deformities of the spine of the patient. The treatment generally involves the step of: correction of the spinal deformity, spinal fusion using bone grafts to bridge gaps, and spinal fixation involving the technology of the present invention.

Figure 1:
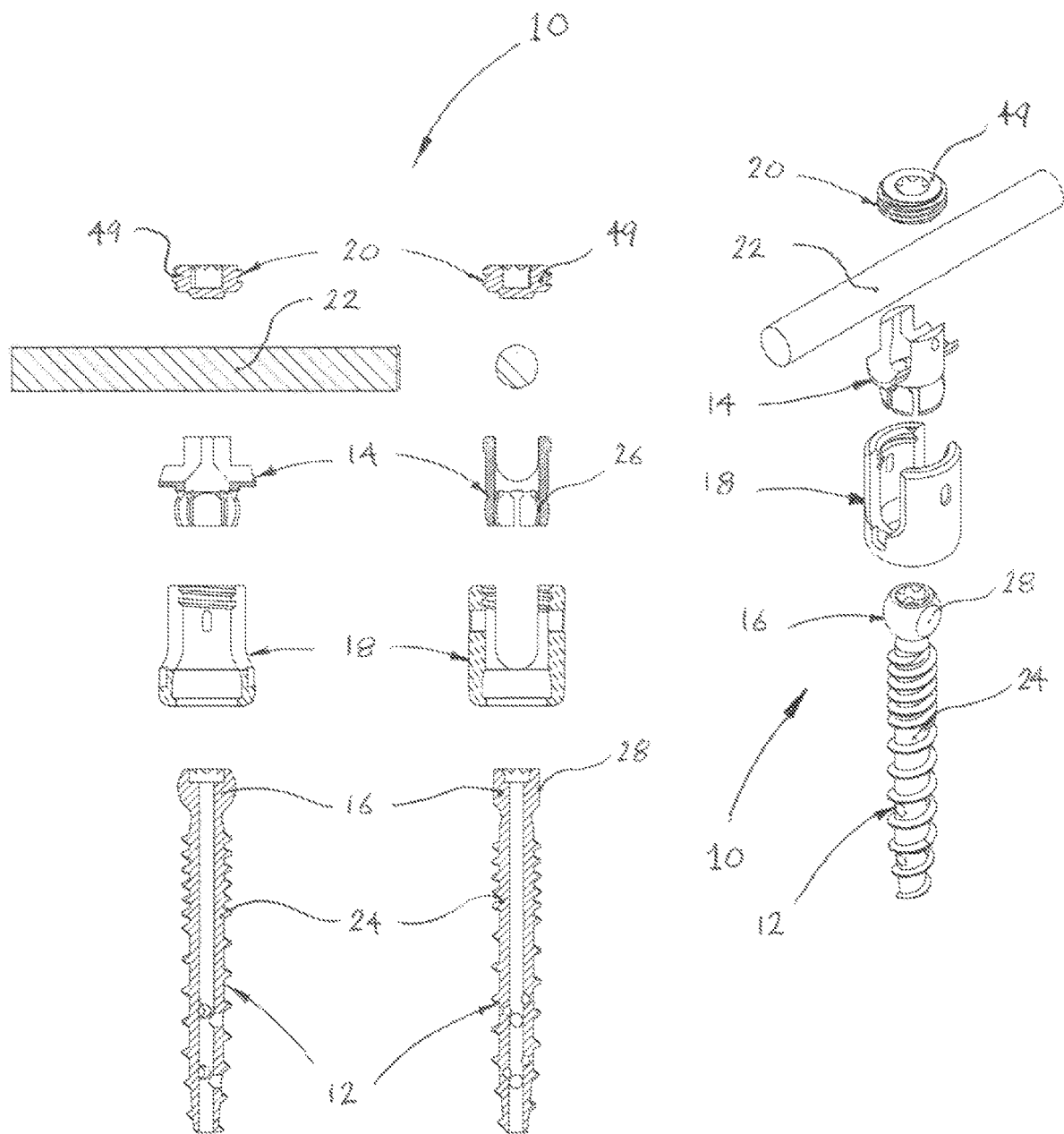
FIG. 1 is an exploded view in perspective and alternative cross-sections of an embodiment of a modular pedicle screw assembly of the invention.
Figure 2:
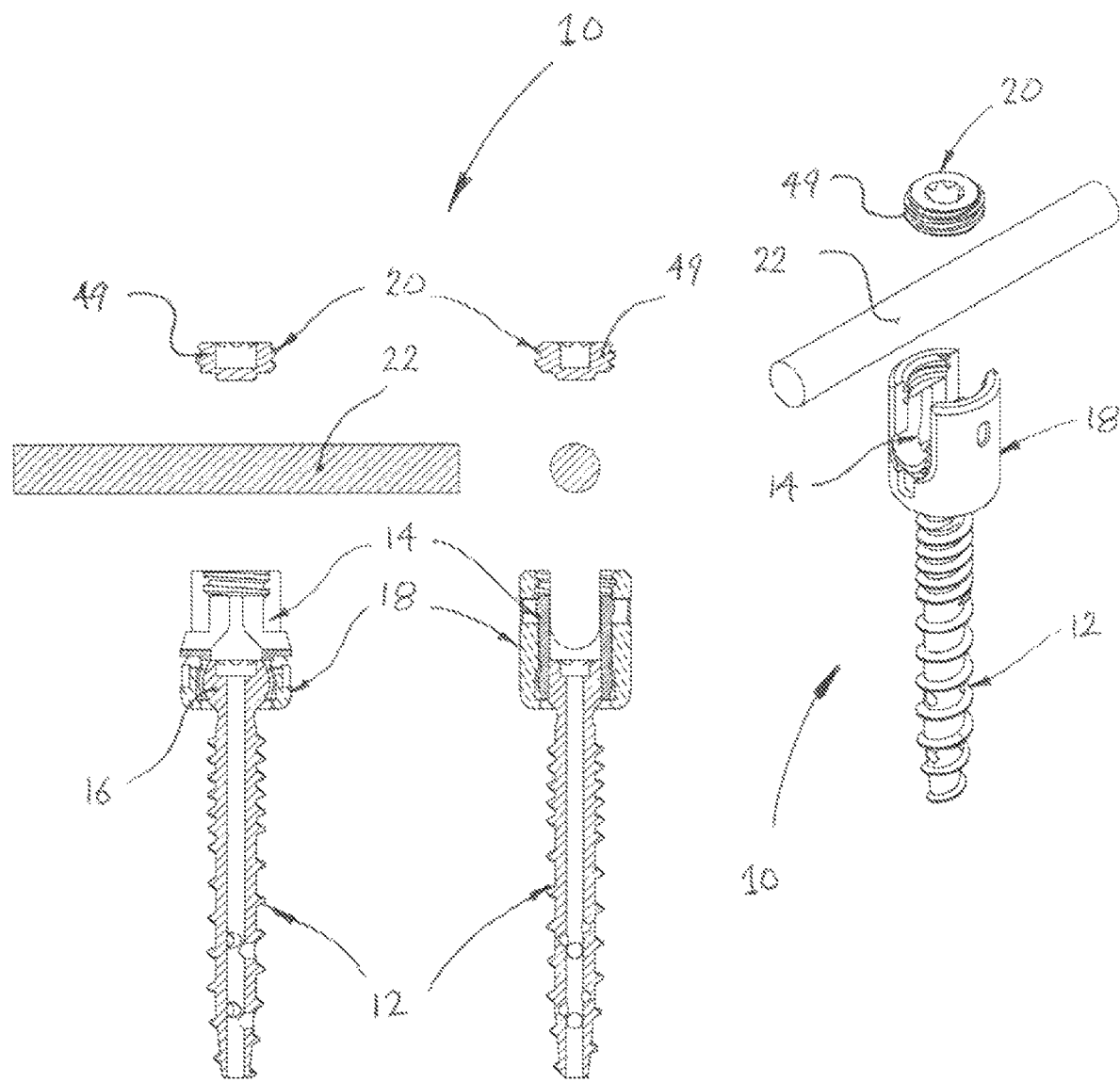
FIG. 2 is part-exploded view in perspective and alternative cross-sections of the modular pedicle screw assembly of FIG. 1.
Figure 3:
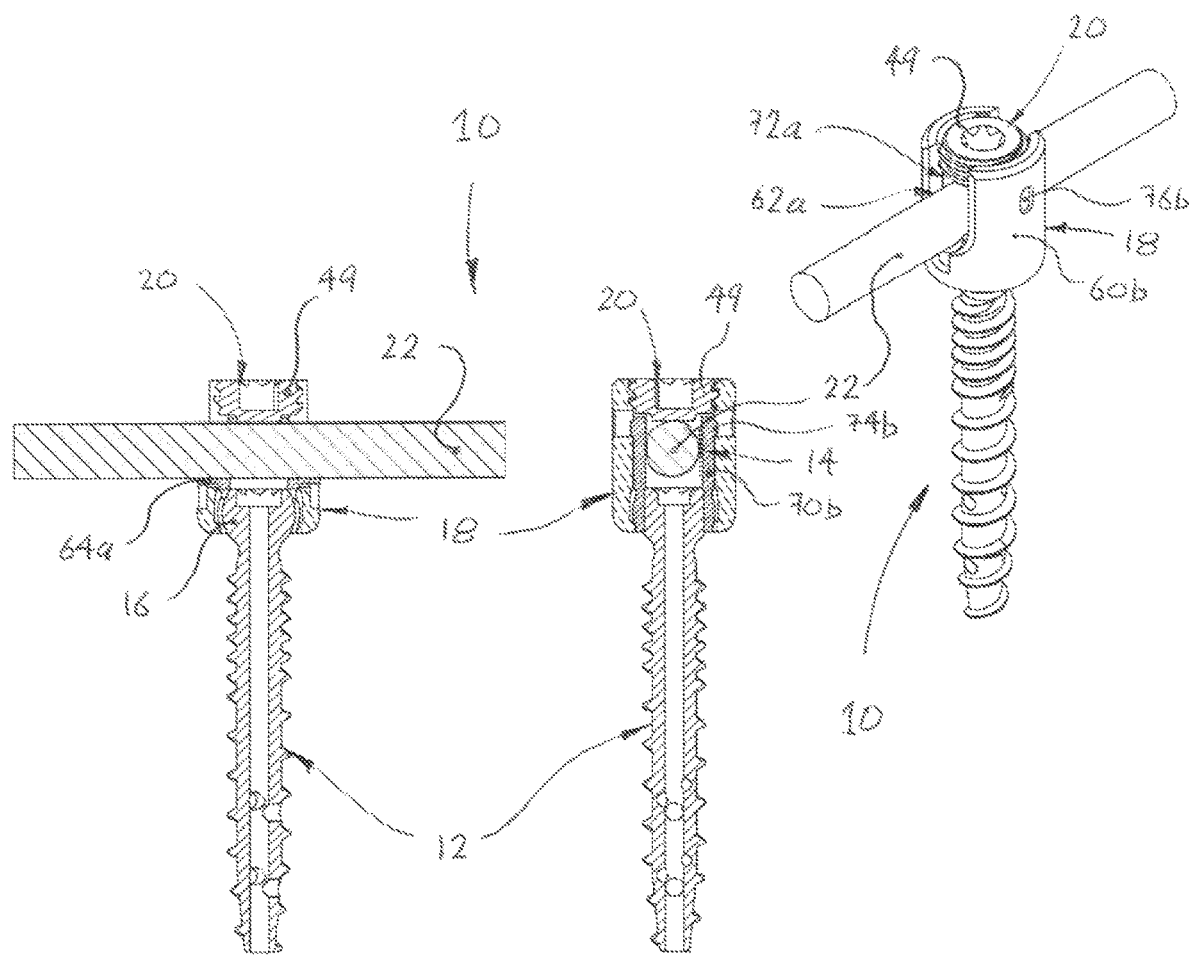
FIG. 3 is an assembled view in perspective and alternative cross-section of the modular pedicle screw assembly of FIGS. 1 and 2.

In the preferred embodiment the modular pedicle screw assembly 10 generally comprises a bone screw 12, a uniaxial inner collet 14 arranged to cooperate with a head 16 of the bone screw 12, a seat 18 arranged to provide seating for retention of the inner collet 14, and an inner collet actuator 20 designed to engage the seat 18 to activate the inner collet 14 for clamping about the head 16 of the bone screw 12. FIG. 1 illustrates the modular pedicle screw assembly 10 in its exploded view or disassembled condition whereas:
1. FIG. 2 depicts the modular pedicle screw assembly 10 in a part assembled condition but for the inner collet actuator 20 and an associated rod 22 retracted from the remainder of the assembly 10;
2. FIG. 3 shows the modular pedicle screw assembly 10 in its fully assembled condition.

It will be understood that the bone screw 12 having a threaded bone shaft 24 is designed for insertion in a vertebrae and more specifically the pedicle of a patient (not shown). The rod 22 is shown in part only with each of its ends truncated and in practice may be straight or shaped to substantially match the required spinal alignment with the rod 22 being anchored to one or more neighbouring modular pedicle screw assemblies (not shown). The modular pedicle screw assemblies such as 10 together with the associated rod such as 22 serve as a temporary fixation to hold the spine in its correct position until bone grafts or other instrumented segments fuse as a bone.

Figure 4:
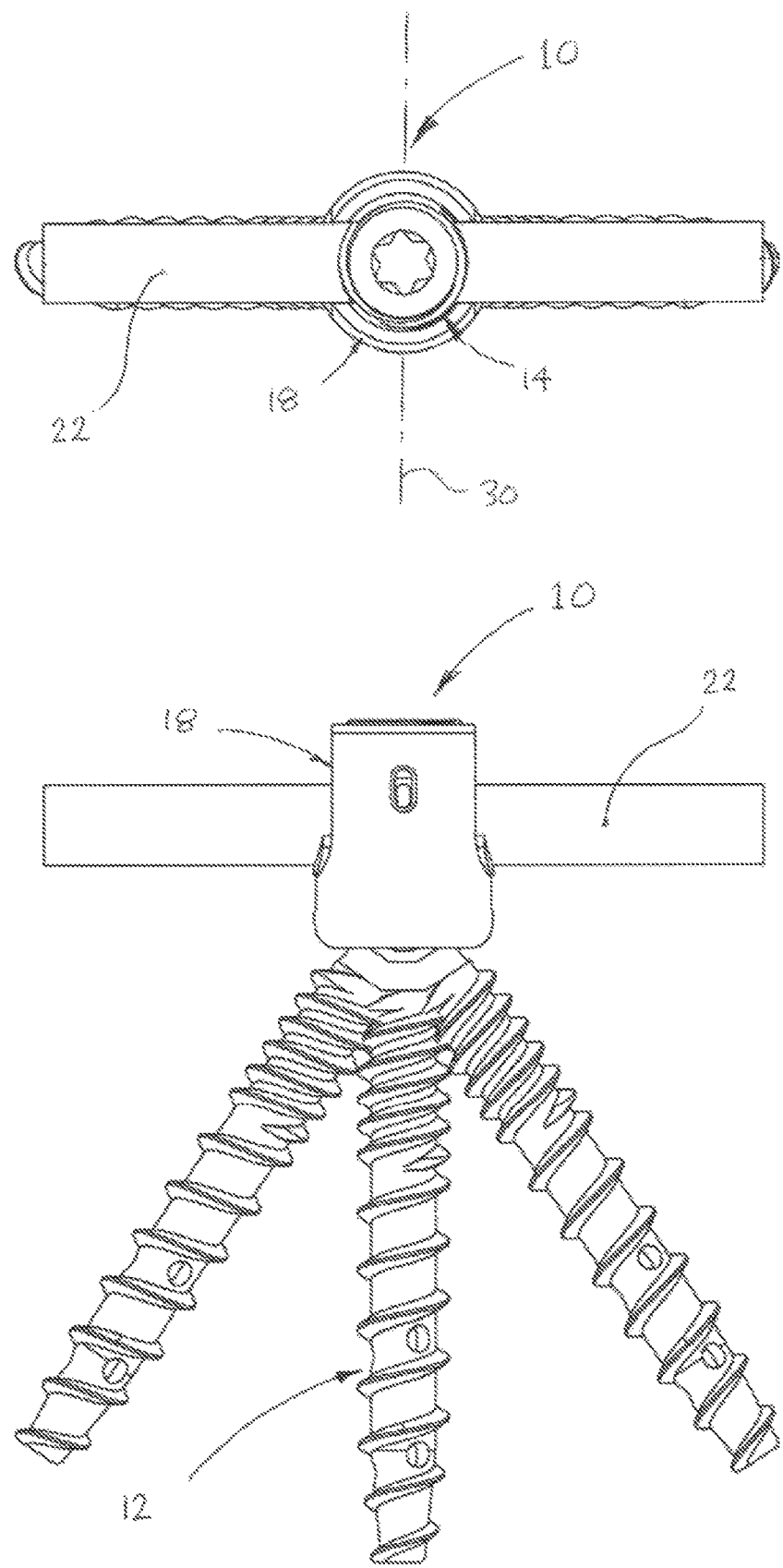
FIG. 4 shows the modular pedicle screw assembly of the preceding figures in plan and side elevation schematically depicting sagittal uniaxial movement appropriate for a coronal imbalance.

The modular pedicle screw assembly 10 is configured depending on the required spinal fixation treatment for the instability or deformity in the patient's spine. The modular pedicle screw assembly 10 of the preferred embodiment of FIGS. 1 to 4 is configured to assist in treating a coronal imbalance in a side-to-side direction of the spine. For this purpose the uniaxial inner collet 14 includes a bearing surface 26 corresponding to a truncated flat surface 28 of the head 16 of the bone screw 12. As schematically seen in FIG. 4, the bearing surface 26 is arranged to permit tilting of the inner collet 14 in an inoperative position about a tilt axis 30 of the head 16 of the bone screw 12. The uniaxial inner collet 14 is seated for retention within the seat 18 at a fixed angular disposition relative to the rod 22. The modular pedicle screw assembly 10 of FIGS. 1 to 4 has the tilt axis 30 oriented substantially perpendicular to the rod 22 which provides uniaxial tilting of the assembly 10 in a sagittal plane suitable for a coronal imbalance.

Figure 5:
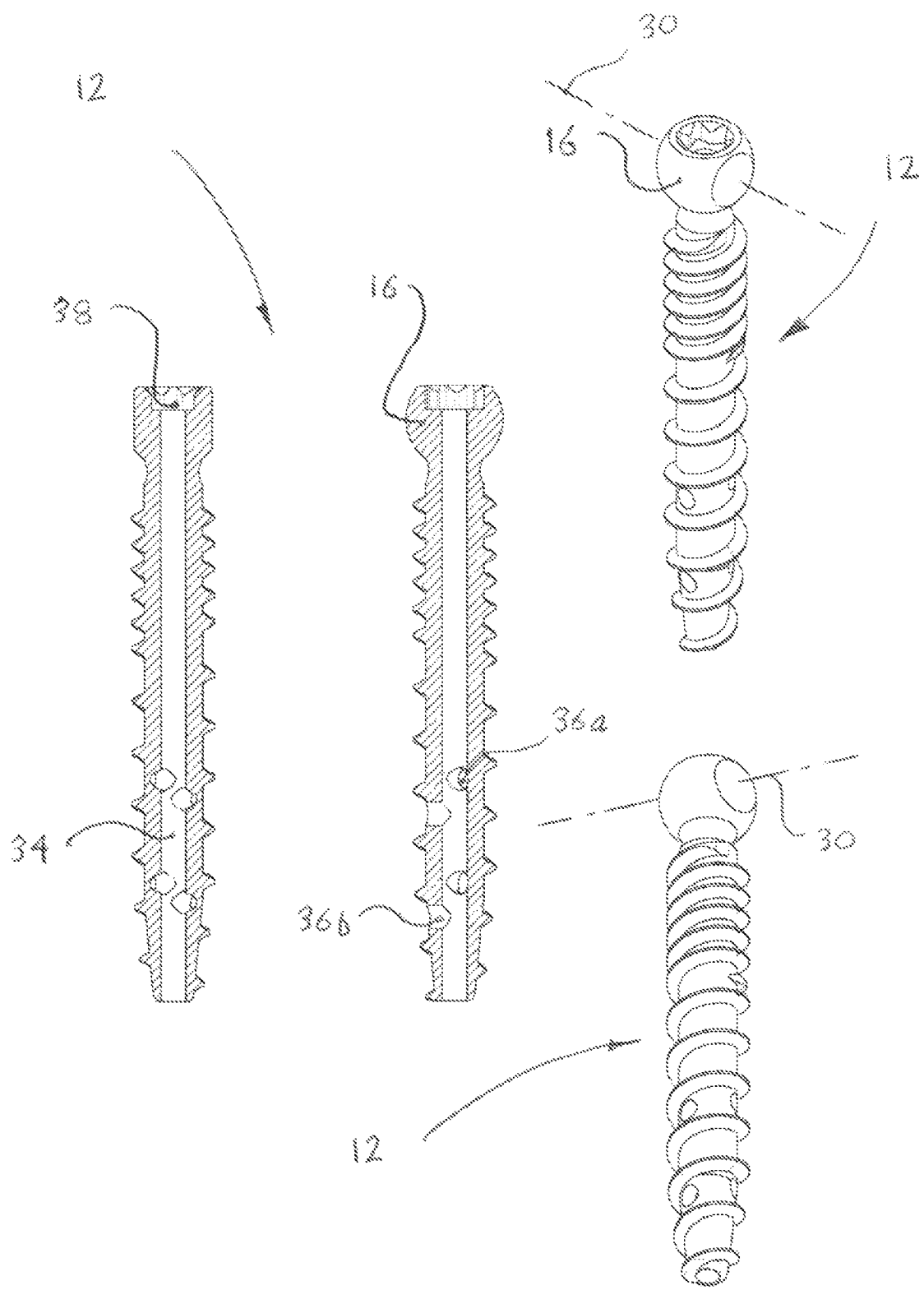
FIG. 5 illustrates alternative perspective and longitudinal sectional views of a bone screw taken from the modular pedicle screw assembly of the preceding figures.

FIG. 5 illustrates the bone screw 12 of the modular pedicle screw assembly 10 of the preferred embodiment of FIGS. 1 to 4. Importantly the ball-shaped head 16 of the bone screw 12 includes the truncated flat surface being one of a pair of opposing truncated flat surfaces 28a and 28b. The pair of truncated flat surfaces 28a and 28b are configured in this embodiment to cooperate with a corresponding pair of bearing surfaces 26a and 26b formed internally of the uniaxial inner collet 14. As seen in FIG. 2, this arrangement permits tilting of the inner collet 14 in its inoperative position in the sagittal plane about the tilt axis 30 of the head 16 of the bone screw 12. Otherwise the bone screw 12 of this embodiment is cannulated with a longitudinal bore 34 and fenestrated with one or more radial apertures such as 36a.

In this embodiment the bone screw 12 is provided in a plurality of predetermined lengths and diameters depending on the requirement. Importantly, each of the various sized bone screws 12 includes a common-sized and shaped head such as 16. The common head 16 having the truncated flat surfaces 28a/b is thus designed to match with the uniaxial inner collet such as 14 of the modular pedicle screw assembly 10 of the preferred embodiment. The applicant intends to colour the:
1. the common ball-shaped head 16 of the bone screw 12 to signify the diameter of the bone screw 12;
2. the threaded bone shaft 24 of the bone screw 12 to signify the length of the bone screw 12.

It should be understood that the smaller diameter bone screws may not be of a sufficient size to permit cannulation in which case the threaded bone shaft 24 is solid without the elongate bore 34 and radial apertures such as 36a/b. Otherwise the head 16 of the bone screw 12 includes a conventional hexagonal-shaped socket 38 for receipt of a tool (not shown) for insertion into the pedicle.

Figure 6:
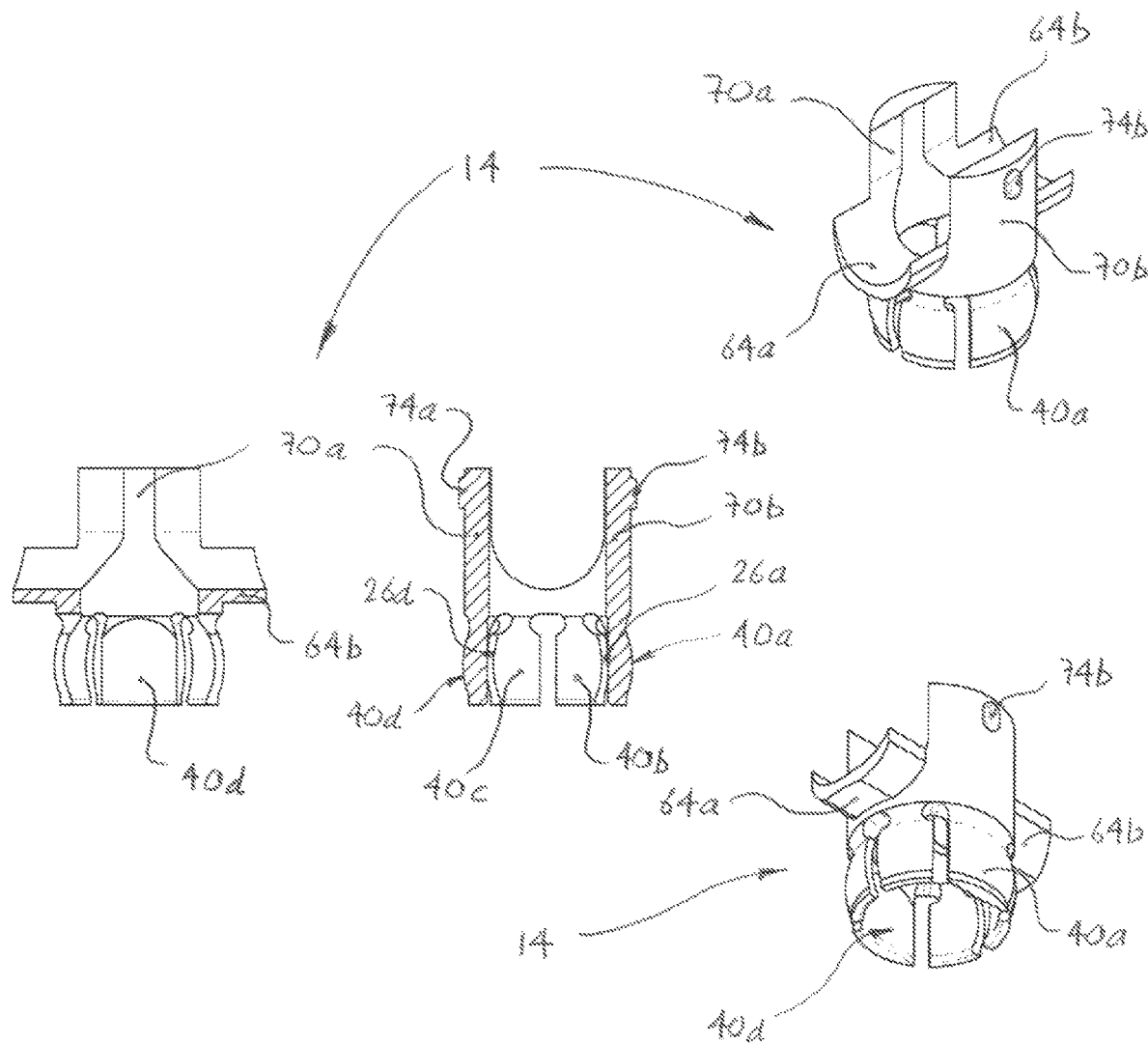
FIG. 6 illustrates alternative perspective and longitudinal sectional views of a uniaxial inner collet taken from the modular pedicle screw assembly of FIGS. 1 to 4.

FIG. 6 shows the uniaxial inner collet 14 in more detail taken from the preferred embodiment of FIGS. 1 to 4. In this example the uniaxial inner collet 14 includes a plurality of claw elements such as 40a to 40f configured in the inoperative position of the inner collet 14 to permit tilting about the head 16 of the bone screw 12. This tilting action is enabled by the opposing pair of flat bearing surfaces 26a and 26b formed internally of respective of the opposing pair of claw elements 40a and 40d. In the inoperative position of the inner collet 14, with tilting of the uniaxial inner collet 14, the bearing surfaces 20a/b of the inner collet 14 slide about the corresponding truncated surfaces 28a/b of the head 16 of the bone screw 12. Clamping of the inner collet 14 to the head 16 of the bone screw 12 in the operative position locks the inner collet 14 to the head 16.

Figure 7:
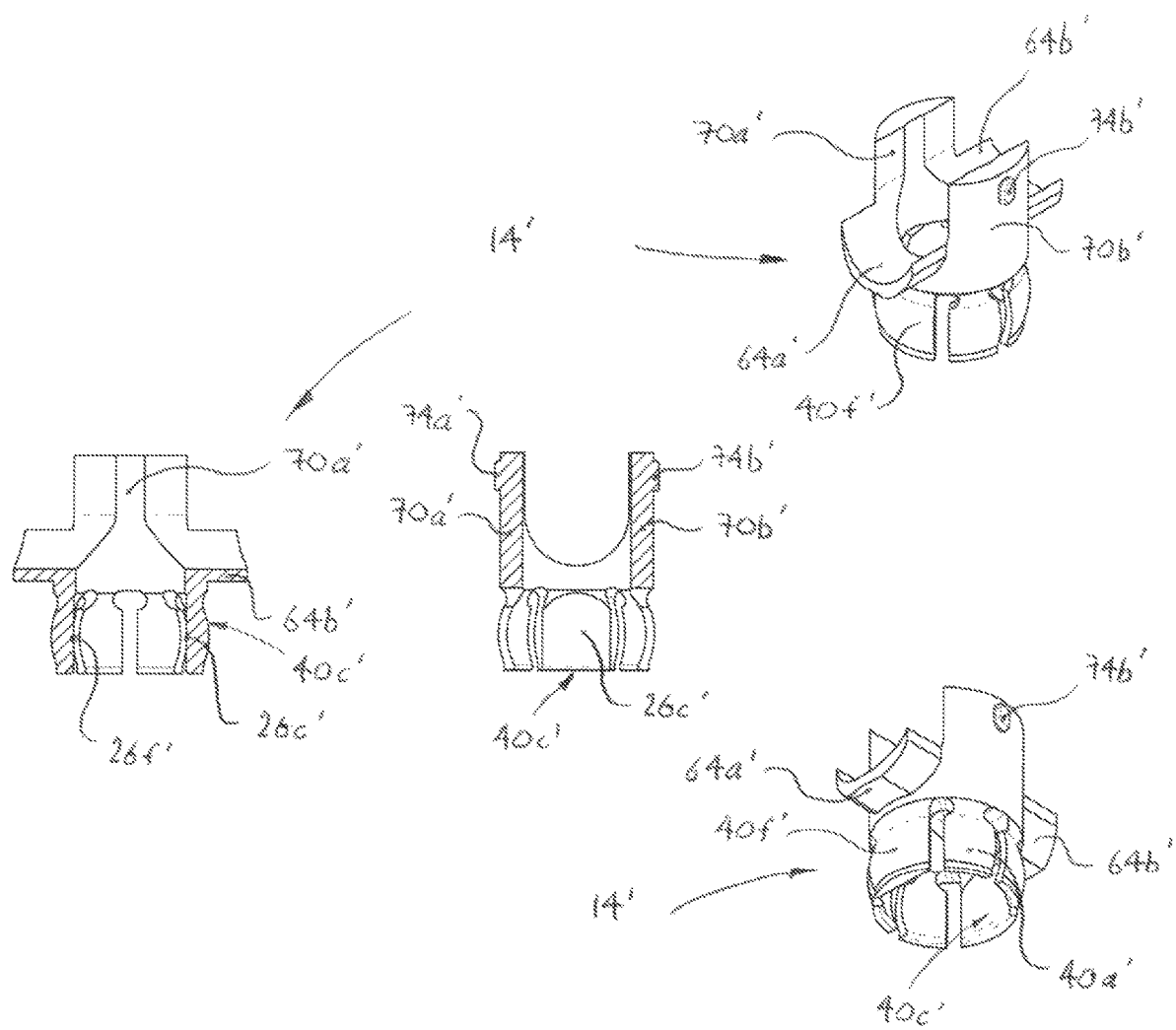
FIG. 7 depicts alternative perspective and longitudinal sectional views of an alternative uniaxial inner collet to substitute for the uniaxial inner collet of FIG. 6 wherein the modular pedicle screw assembly is appropriate for a sagittal imbalance.
Figure 8:
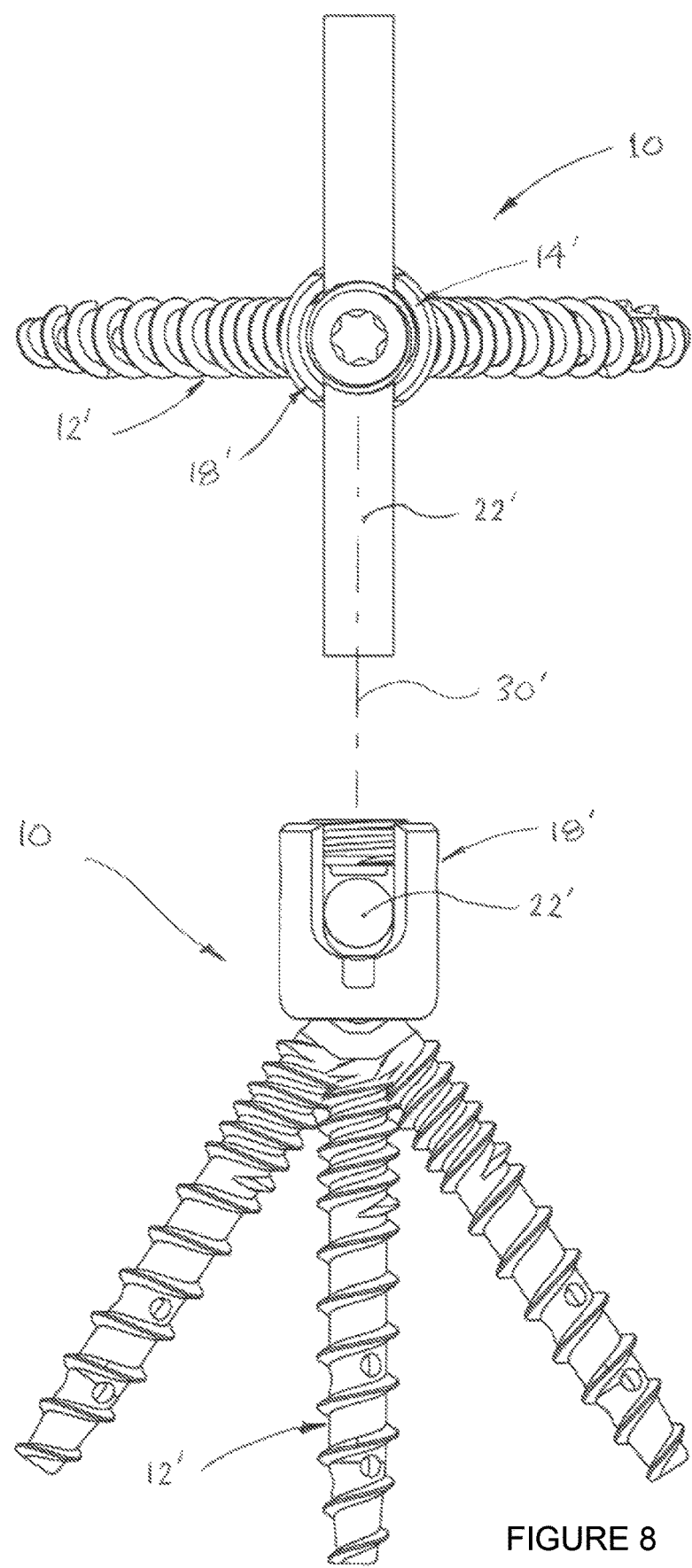
FIG. 8 illustrates in plan and side elevation the modular pedicle screw assembly with the uniaxial inner collet of FIG. 7 fitted schematically depicting uniaxial movement of the modular pedicle screw assembly.

FIG. 7 depicts an alternative uniaxial inner collet 14' which is substantially identical to the inner collet 14 of the preceding embodiment except for location of the opposing bearing surfaces 26a' and 26b'. The surfaces 26a'/b' reconfigure the modular pedicle screw assembly 10 for uniaxial movement but with the tilt axis 30 of the head 16 of the bone screw 12 substantially aligned with the rod 22, see FIG. 8. For ease of reference and in order to avoid repetition, the same reference numerals have been used for corresponding components of the alternative uniaxial inner collets 14 and 14'. It will be understood that the modular pedicle screw assembly 10 with the substitute uniaxial inner collet 14' is suited to treatment of a sagittal imbalance such as a kyphosis or lordosis being a front-to-back spinal curvature. In this alternative uniaxial configuration, the screw assembly 10 is designed to tilt in a transverse plane being approximately orthogonal to the sagittal plane.

Figure 9:
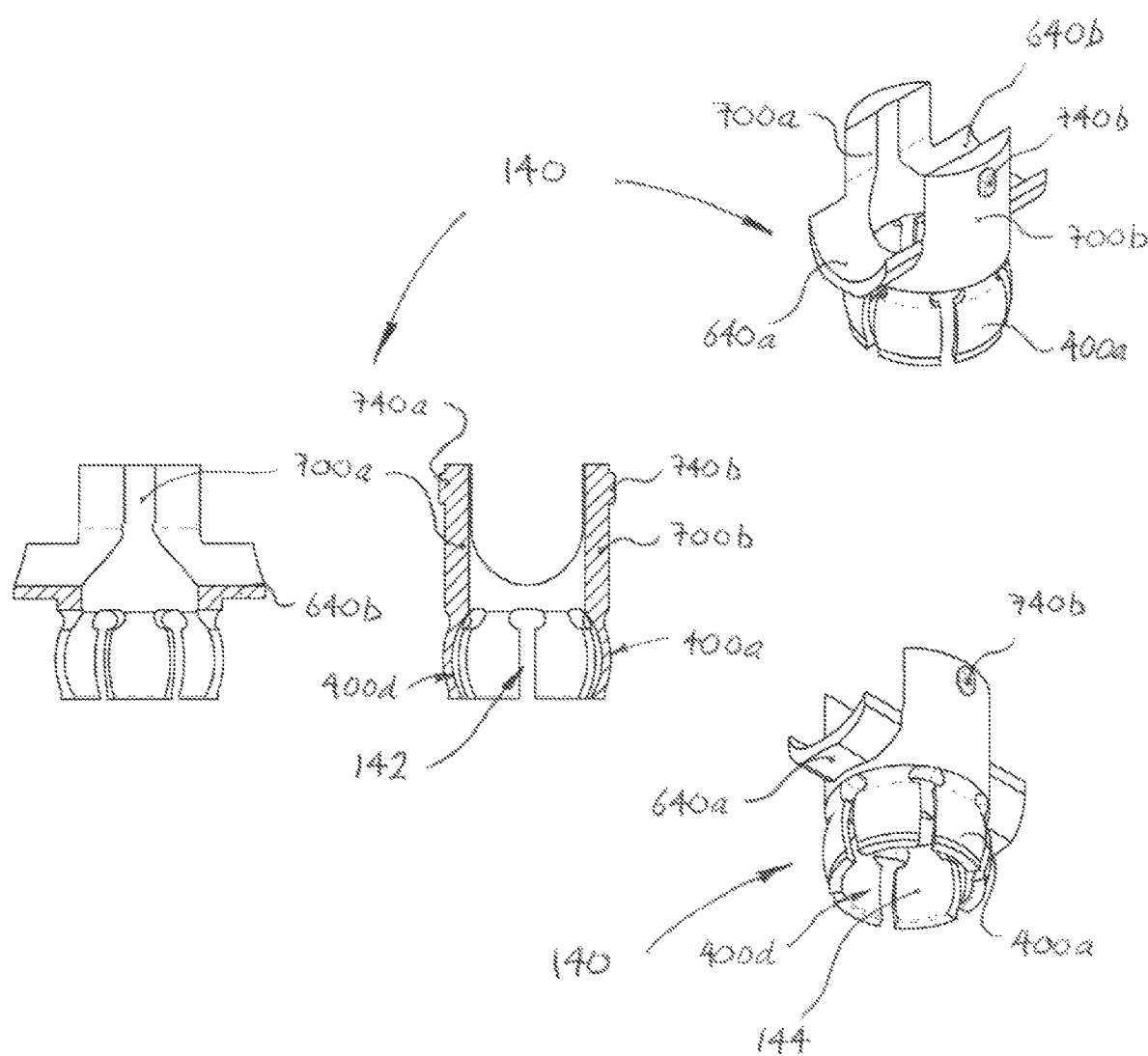
FIG. 9 shows alternative perspective and longitudinal sectional views of a polyaxial inner collet to substitute for either of the uniaxial inner collets of FIG. 6 or 7 wherein the modular pedicle screw assembly permits polyaxial movement.

FIG. 9 illustrates a polyaxial inner collet 140 configured to substitute for either of the uniaxial inner collets 14 or 14' in the modular pedicle screw assembly 10. The polyaxial inner collet 140 is substantially identical to the uniaxial inner collets 14/14' except it does not include the opposing bearing surfaces such as 26a/b but rather each of the plurality of claw elements 400a to 400f is of an identical shape. This means the polyaxial inner collet 140 includes a cavity 142 defining an internal surface 144 configured to permit polyaxial movement of the inner collet 140 in the inoperative position about the head 16 of the bone screw 12. The polyaxial inner collet 140 is otherwise of the same construction as the uniaxial inner collets 14/14' wherein the claw elements 400a to 400f of the inner collet 140 in the operative position clamp about the head 16 of the bone screw 12 for locking to the bone screw 12.

Figure 10:
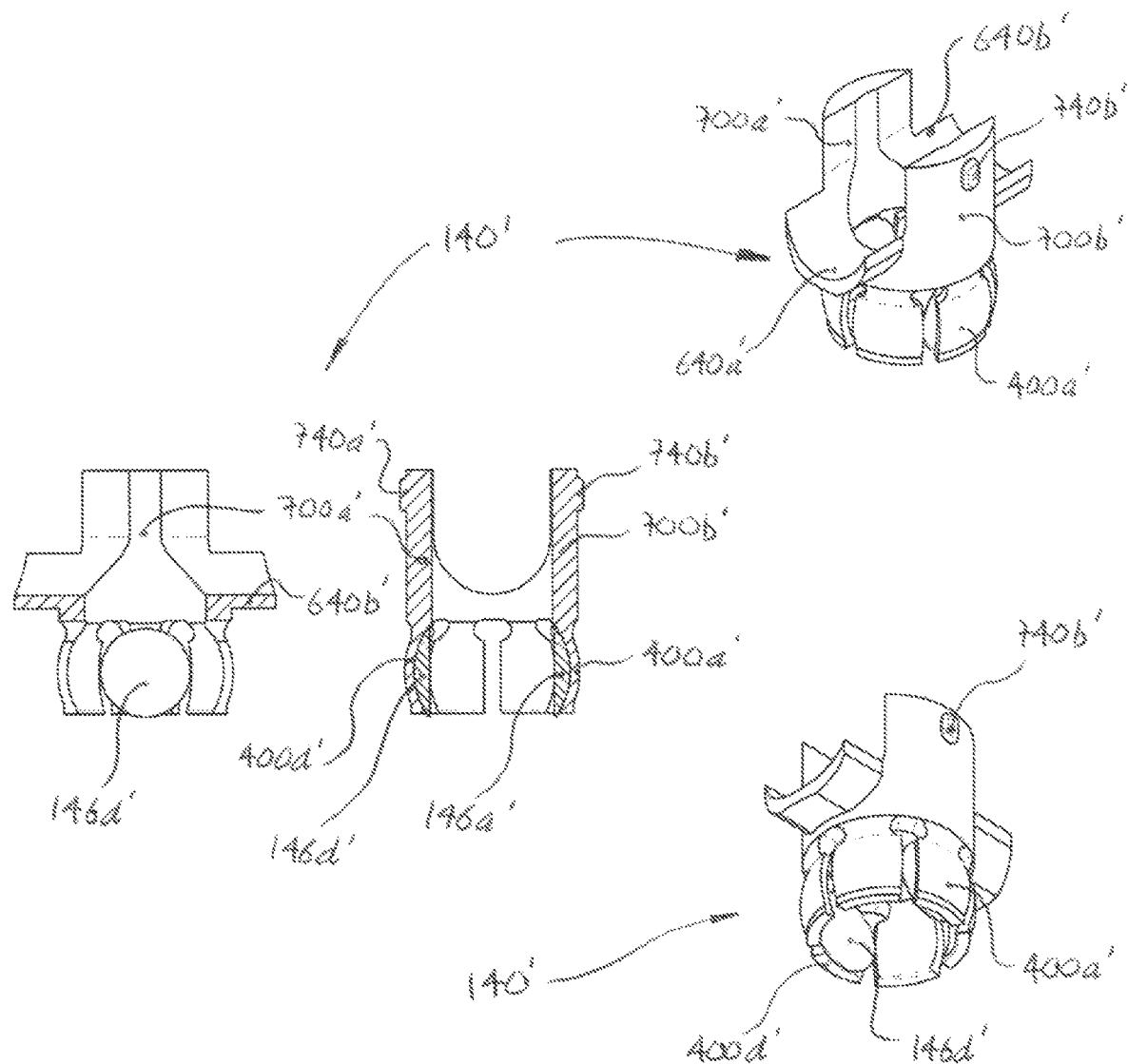
FIG. 10 depicts alternative perspective and longitudinal sectional views of a variation on the polyaxial inner collet of FIG. 9 to substitute for either of the uniaxial inner collets of FIG. 6 or 7.

FIG. 10 depicts a variation on the polyaxial inner collet 140 of FIG. 9. In this variation, the polyaxial inner collet 140' includes a pair of inserts 146a' and 146d' frangibly connected to respective of the opposing pair of claw elements 400a' and 400d' of the inner collet 140'. Each of the inserts such as 146a' is in the form of a filler chamfer designed at a predetermined force to release from the respective claw element such 400a' to locate at the truncated flat surface 28a of the head 16 of the bone screw 12. The polyaxial inner collet 140' of this variation is thus mobilised in the inoperative position for polyaxial movement about the head 16 of the bone screw 12. The polyaxial inner collet 140' in the operative position clamps about the head 16 of the bone screw 12 with the pair of inserts or filler chamfers such as 146a' increasing the effective clamping surface of the head 16 exposed to the plurality of claws such as 400a' to 400f' of the inner collet 140'. This means the polyaxial inner collet 140' is less likely to pull out from the head 16 of the associated bone screw 12.

Figure 11:
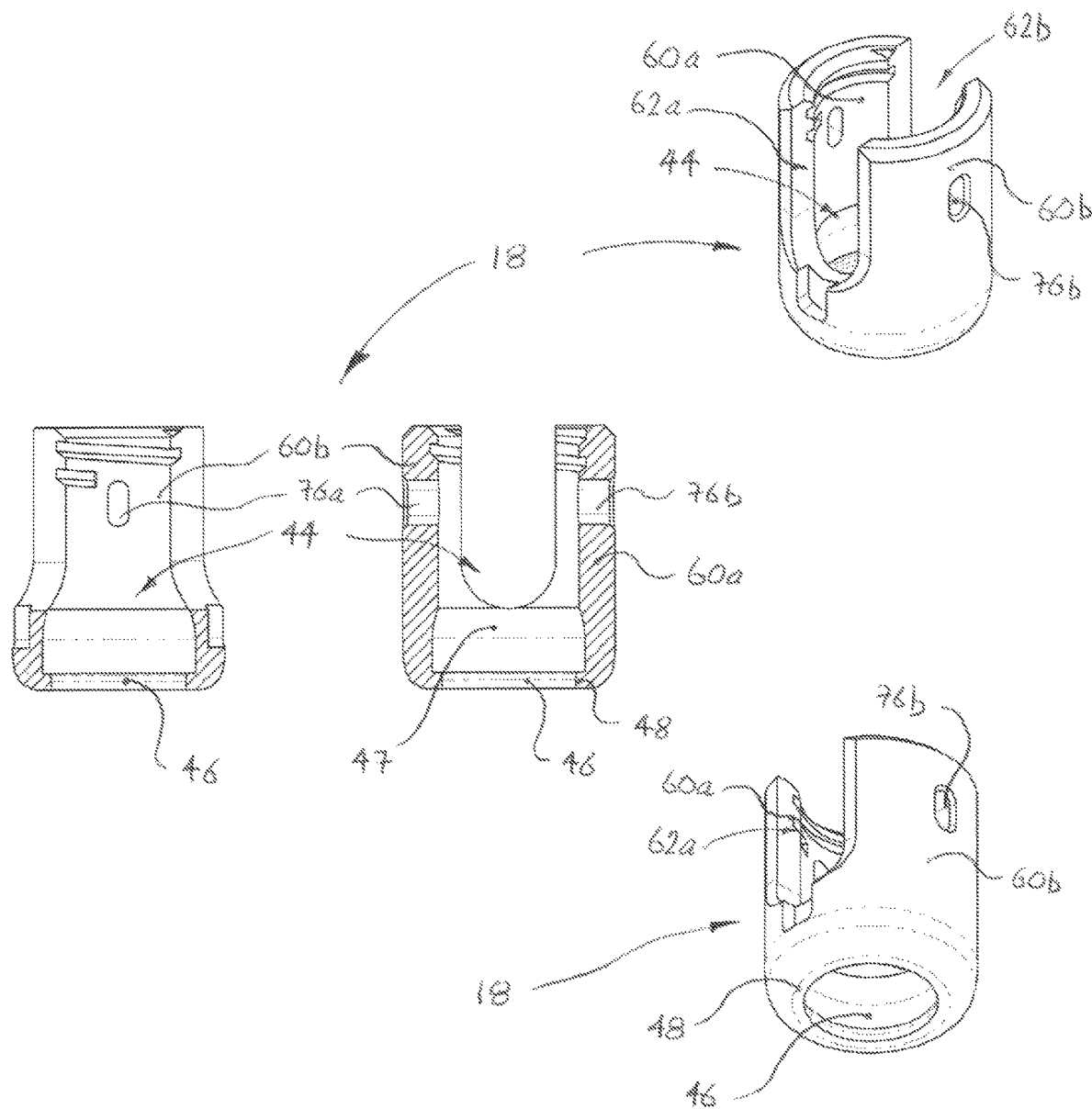
FIG. 11 shows alternative perspective and longitudinal sectional views of a seat taken from the modular pedicle screw assembly of FIGS. 1 to 4.

FIG. 11 illustrates the seat or head 18 taken from the modular pedicle screw assembly 10 of the preferred embodiment of FIGS. 1 to 4. The seat 18 is designed in a general sense to provide seating for retention of the inner collet such as 14 which in the inoperative position tilts about the head 16 of the bone screw 12 in conjunction with the seat 18. In this embodiment the seat 18 includes a recess 44 within which the inner collet such as 18 seats for activation via the inner collet actuator 20. The inner collet 14 is thus moveable via the inner collet actuator 20 from:

1. the inoperative position where the head 16 of the bone screw 12 is received within the inner collet 14 with radial separation of the claw elements such as 40a to 40f of the inner collet 14 into the recess 44 of the seat 18;

2. the operative position where the head 16 of the bone screw 12 is locked within the inner collet 14 with clamping of the claw elements 40a to 40f about the head 16 of the bone screw 12.

In this embodiment the seat 18 includes an aperture 46 formed continuous with the recess 44 and arranged for receipt of the head 16 of the bone screw 12. The head 16 of the bone screw 12 is thus received into the inner collet 14 which is retained in the inoperative position for seating in the recess 44 of the seat 18. The recess 44 of the seat 18 includes annular rebate 47 configured, with the inner collet 14 in the inoperative position, to permit the radial separation of the claw elements 40a to 40f into the annular rebate 46 on receipt of the head 16 of the bone screw 12 into the inner collet 14. The seat 18 also includes an annular flange 48 defining the aperture 46 through which the head 16 of the bone screw 12 is received. The flange 48 is configured with the inner collet 14 in the operative position to urge the claw elements 40a to 40f of the inner collet 14 for clamping about the head 16 of the bone screw 12.

Figure 12A:
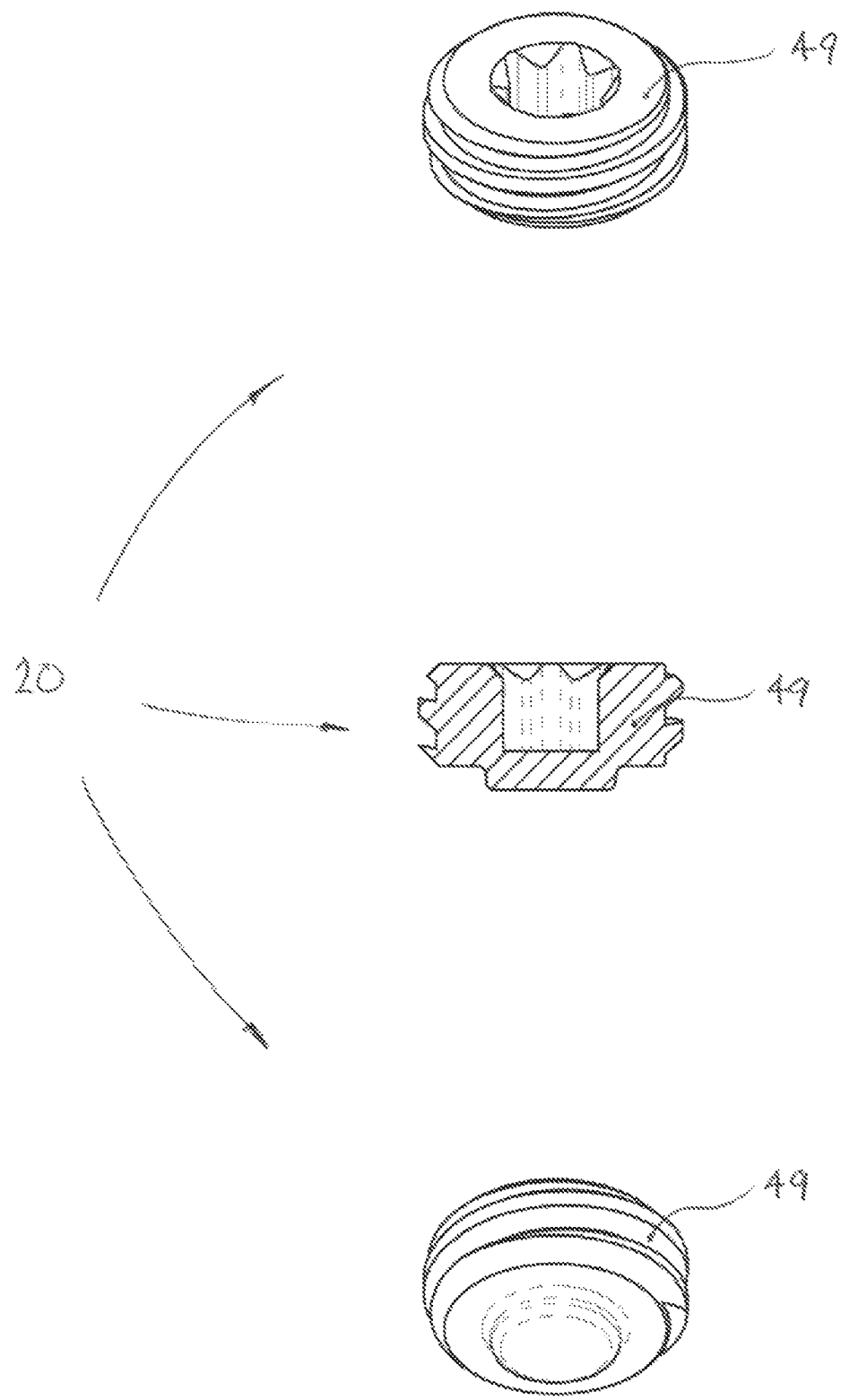
FIGS. 12A and 12B show perspective and sectional views of alternative embodiments of an inner collet actuator and locking element suited to the modular pedicle screw assembly of FIGS. 1 to 4.
Figure 12B:
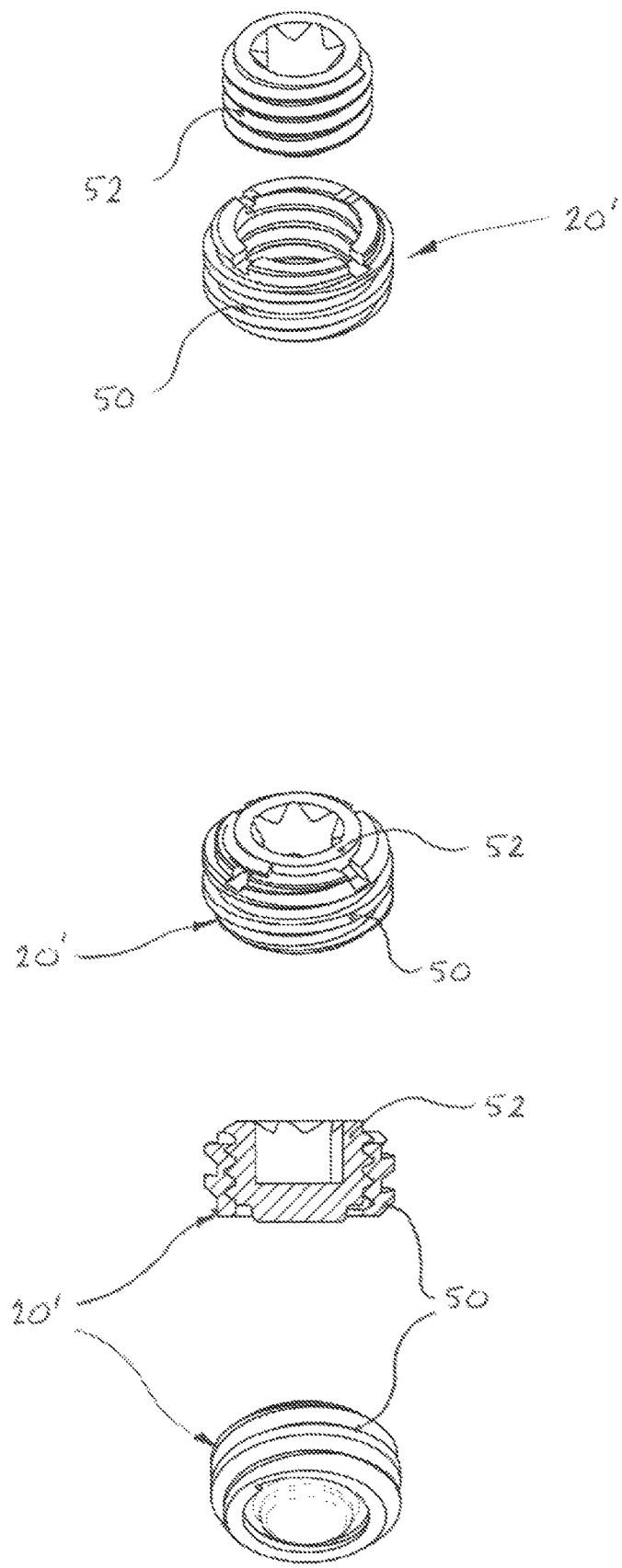

FIG. 12A shows the inner collet actuator 20 taken from the preferred embodiment of the modular pedicle screw assembly 10 of FIGS. 1 to 4. The inner collet actuator 20 is integral with a locking element and together they are provided in the form of a unitary set screw 49. The unitary set screw 49 threadably engages the seat 18 for both activation of the inner collet 14 and locking of the rod 22 to the seat 18. The unitary set screw 49 includes a hexagonal-shaped socket 51 for receipt of a tool (not shown) for applying a torque load to the set screw 49. In an alternative embodiment seen in FIG. 12B, the locking element functions independent of the inner collet actuator 20'. The inner collet actuator 20' is in the form of an external set screw 50 arranged to threadably engage the seat 18 for activation of the inner collet 14. The locking element is in the form of an internal set or grub screw 52 arranged to threadably engage the external set screw 50. The grub screw 52 thus operates independent of the external set screw 50 for locking of the rod 22 to the seat 18.

Returning to FIG. 11, it can be seen that the seat 18 includes a pair of legs 60a and 60b defining a pair of opposing and axially oriented channels 62a and 62b. The channels 62a/b are arranged to receipt of the rod 22 for locking to the seat 18 via the locking element 49. As seen in FIG. 6, the inner collet 14 includes a pair of radially extending arms 64a and 64b aligned with one another and arranged for seating within the pair of opposing channels 62a and 62b of the seat 18. The rod 22 is thus oriented at a fixed angular disposition relative to the tilt axis 30 of the head 16 of the bone screw 12. It will be appreciated that this angular disposition is determined by the angular position of the flat bearing surfaces 26a/b of the uniaxial inner collet 14 relative to the pair of radially extending arms 64a/b.

In the preferred embodiment having the uniaxial inner collet 14 of FIG. 6, the arms 64a/b are oriented directionally parallel with the bearing surfaces 26a/b of the inner collet 14 wherein the rod 22 is disposed perpendicular with the tilt axis 30 of the head 16 of the bone screw 12 about which the inner collet 14 in the inoperative position is arranged to tilt. This configuration of the modular pedicle screw assembly 10 is suited to spinal fixation for treatment of a coronal imbalance where the screw assembly 10 tilts in the sagittal plane. Alternatively, the uniaxial inner collet 14' of FIG. 7 may be fitted to the modular pedicle screw assembly 10. In this case the radial arms 64a'/b' of the uniaxial inner collet 14' are directionally perpendicular with the bearing surface 26a'b' of the inner collet 14' wherein the rod 22 is disposed substantially parallel with the tilt axis 30 of the head 16 of the bone screw 12. In this configuration the modular pedicle screw assembly 10 is suited to spinal fixation for treating a sagittal imbalance such as a kyphotic deformity and the screw assembly 10 tilts in the transverse plane.

As best seen in the uniaxial inner collets 14 and 14' of FIGS. 6 and 7 as well as the polyaxial inner collets 140 and 140' of FIGS. 9 and 10, the inner collet such as 14 includes a pair of legs 70a and 70b disposed either side of the pair of radially extending arms 60a and 60b. The legs 70a/b define a pair of opposing and axially oriented channels 72a/b arranged for receipt of the rod 22. As best seen in FIG. 3, the pair of channels 72a/b of the inner collet 14 substantially align with the channels 62a/b of the seat 18. Each of the legs such as 70b of the inner collet 14 include a protrusion such as 74b for releasable retention within a corresponding opening such as 76b in the corresponding leg 60b of the seat 18. The protrusion 74b is in the form of a nipple designed to retain the inner collet 14 within the seat 18 in both the inoperative and operative positions.

FIGS. 1 to 3 best illustrate the sequence of events for assembly of the modular pedicle screw 10 of this embodiment of the invention. It will be understood that, although not illustrated, the bone screw 12 is typically inserted into the pedicle (not shown) identified for instrumentation prior to assembly of the modular pedicle screw 10. This step is repeated for other pedicles that have been identified for similar instrumentation. The assembly of the remainder of the modular pedicle screw assembly 10 involves the following steps:

1. an inner collet is selected from one of the uniaxial 14/14' or polyaxial 140/140' inner collets depending on the required treatment, such as that required for a coronal or sagittal imbalance;
2. the selected collect such as 14 is loaded within the seat 18, the inner collet 14 being retained in the seat 18 via its protrusions such as 74b with its radial arms such as 64a seated within opposing channels such as 62a of the seat 18;
3. the seat 18 and associated inner collet 14 are pressed over the head 16 of the bone screw 12, aligning the bearing surfaces such as 26a with the corresponding truncated surfaces such as 28a of the head 16 of the bone screw 12;
4. the inner collet in the inoperative position being slightly raised relative to the seat 18 expands about the head 16 of the bone screw 12 for receipt of the head 16;
5. the inner collet 14 in the inoperative position resiliently contracts about the head 16 of the bone screw 12 for its retention;
6. the rod 22 is loaded into the aligned channels such as 62a and 72a of the seat 18 and the inner collet 14, respectively, with any relatively small rotation of the bone screw 12 for the uniaxial inner collets 14 being made via an appropriate tool;
7. the inner collet actuator 20 and locking element are screwed into the seat 18 for simultaneous i) activation or movement of the inner collet 14 into the operative position for clamping about the head 16 of the bone screw 12 to lock the inner collet 14 and the seat 18 to said head 16, and ii) locking of the rod 22 to the seat 18.

The inner collet actuator 20 or unitary set screw 49 of this embodiment threadably engages the legs such as 60a of the seat 18 for contact with the inner collet 14 to effect its movement in a sliding action from the inoperative position to the operative position. In the operative position the annular flange 48 of the seat 18 contacts the claw elements such as 40a to 40f of the inner collet 14 for clamping about the head 16 of the bone screw 12 with increasing pressure. When the inner collet 14 is clamped about the head 16 of the bone screw 12 with sufficient locking pressure, the radially extending arms such as 64a of the inner collet 14 are arranged to rest at a base of the respective channels such as 62a of the seat 18 within which they are seated. In this example the openings such as 76a of the legs 60a of the seat 18 are formed as longitudinal slots so that the protrusion such as 74a of the inner collet 14 is retained for sliding movement within the corresponding slots such as 76a during movement of the inner collet 14 between the inoperative and operative positions.

In further aspects of the invention there is provided a uniaxial pedicle screw sub-assembly or assembly. In these aspects the sub-assembly or assembly need not be of a modular construction. In both aspects the sub-assembly or assembly is limited to a uniaxial inner collet with uniaxial tilting of the inner collet and the associated seat about a tilt axis of the head of the associated bone screw. The sub-assembly or assembly may take the form of the embodiment of FIGS. 1 to 4 but with the inner collet and seat permanently mounted to the head of the bone screw. It will be understood that the uniaxial pedicle screw sub-assembly or assembly may also tilt in an orthogonal plane to that of this embodiment. These other aspects of the non-modular screw sub-assembly or assembly are inserted into the vertebrae or pedicle with the inner collet and seat in-situ.

Now that several preferred embodiments of the modular pedicle screw assembly have been described it will apparent to those skilled in the art that they have the following advantages:

1. the modular assembly shares common or universal components, with the exception of the inner collet and the bone screw, thereby reducing costs for spinal surgeons in maintaining sufficient stock;
2. the uniaxial and polyaxial assemblies rely upon a common sized and shaped head for the bone screw minimising the range of bone screws required;
3. the modular pedicle screw assembly can be reconfigured for either uniaxial or polyaxial movement by selecting a uniaxial or polyaxial inner collet;
4. the uniaxial pedicle screw sub-assembly or assembly can be easily configured for application in a coronal or sagittal imbalance by selecting the appropriate uniaxial inner collet;
5. the modular pedicle screw assembly in its polyaxial configuration is designed with increased clamping about the head of the associated bone screw to reduce the likelihood of pull out.

Those skilled in the art will appreciate that the invention as described herein is susceptible to variations and modifications other than those specifically described. For example, the specific construction of the inner collet and/or the seat of the modular pedicle screw assembly may vary from the preferred embodiment provided selection of either a uniaxial or polyaxial inner collet is effective in reconfiguration of the assembly. The pair of bearing and truncated surfaces on the inner collet and the head of the bone screw, respectively, may be limited to a single bearing surface and corresponding truncated surface on the head of the bone screw. The truncated surface on the head of the bone screw may not be flat provided it complements a corresponding bearing surface in the inner collet which permits uniaxial tilting about a tilt axis of the head of the bone screw.

All such variations and modifications are to be considered within the scope of the present invention the nature of which is to be determined from foregoing description.

The invention claimed is:

1. A modular pedicle screw assembly comprising:
a bone screw having a threaded bone shaft adapted for insertion in a vertebra;
a polyaxial inner collet configured in an operative position to clamp about a head of the bone screw, said head being substantially ball-shaped with a truncated surface wherein the polyaxial inner collet includes a cavity defining an internal surface configured to permit polyaxial movement of the polyaxial inner collet in an inoperative position about the head of said bone screw;
a seat arranged to provide seating for retention of the polyaxial inner collet, the seat designed to move polyaxially in conjunction with the polyaxial inner collet in the inoperative position about the head of said bone screw;
an insert frangibly connected to the polyaxial inner collet to release from said polyaxial inner collet and locate at the truncated surface of the head of the bone screw, the polyaxial inner collet in i) the inoperative position thus being mobilized for polyaxial movement about the head of the bone screw, and ii) in the operative position arranged for clamping about the head of the bone screw having its effective clamping surface increased by the insert located at the truncated surface of said screw head; and
an inner collet actuator configured to engage the seat and operable to activate the polyaxial inner collet for movement into the operative position for clamping about the head of the bone screw to lock the polyaxial inner collet and the seat to the head of said bone screw.

2. A modular pedicle screw assembly as claimed in claim 1 wherein the polyaxial inner collet includes a plurality of claw elements and the insert is one of a pair of inserts frangibly connected to respective of an opposing pair of the plurality of claw elements of the polyaxial inner collet.

3. A modular pedicle screw assembly as claimed in claim 2 wherein the seat includes a recess within which the polyaxial inner collet seats for retention in either the inoperative or operative positions, the polyaxial inner collet being movable via the inner collet actuator from i) the inoperative position where the head of the bone screw is received within the polyaxial inner collet with radial separation of the claw elements of the polyaxial inner collet into the recess of the seat, to ii) the operative position where the head of the bone screw is clamped within the polyaxial inner collet with clamping of the claw elements about the head of the bone screw.

4. A modular pedicle screw assembly as claimed in claim 3 wherein the seat includes an aperture formed continuous with the recess and arranged for receipt of the head of the bone screw into the polyaxial inner collet which is retained in the inoperative position for seating in the recess of the seat.

5. A modular pedicle screw assembly as claimed in claim 4 wherein the recess of the seat includes an annular rebate configured, with the polyaxial inner collet in the inoperative position, to permit the radial separation of the claw elements of the polyaxial inner collet into the annular rebate on receipt of the head of the bone screw into the polyaxial inner collet.

6. A modular pedicle screw assembly as claimed in claim 4 wherein the seat includes an annular flange defining the aperture through which the head of the bone screw is received, said flange configured with the polyaxial inner collet in the operative position to urge the claw elements of the inner collet for clamping about the head of the bone screw.

7. A modular pedicle screw assembly as claimed in claim 1 also comprising a rod for securement to the seat.

8. A modular pedicle screw assembly as claimed in claim 7 further comprising a locking element operatively coupled to the seat to lock the rod to the seat.

9. A modular pedicle screw assembly as claimed in claim 8 wherein the inner collet actuator serves as the locking element, wherein the inner collet actuator is in the form of a set screw arranged to engage the seat for activation of the polyaxial inner collet and to lock the rod to the seat.

10. A modular pedicle screw assembly as claimed in claim 8 wherein, the inner collet actuator is independent of the locking element, wherein the inner collet actuator is in the form of an external set screw arranged to engage the seat for activation of the polyaxial inner collet, and the locking element is in the form of an internal set screw arranged to engage the external set screw for locking of the rod to the seat.

11. A modular pedicle screw assembly as claimed in claim 10 wherein the external set screw includes a threaded aperture within which the internal set screw is received for independent locking of the rod to the seat.

12. A method of assembling a modular pedicle screw assembly, said method comprising the operations:
selecting an inner collet from a plurality of inner collets including at least a uniaxial inner collet having a bearing surface, and a polyaxial inner collet frangibly connected to an insert;
loading the selected inner collet within a seat for retention within said seat;
pressing the selected inner collet and the associated seat over a common-shaped head of a bone screw selected from a plurality of bone screws of different shaft diameters and/or lengths, the common-shaped head for each of the plurality of bone screws being (a) ball-shaped with a truncated surface and (b) of substantially the same size and shape;
receiving the common-shaped head of the selected bone screw within the selected inner collet for uniaxial or polyaxial movement depending on whether the selected collet is the uniaxial inner collet or the polyaxial inner collet, said uniaxial movement being enabled by tilting of the said uniaxial inner collet about the head of the selected bone screw wherein the bearing surface of the uniaxial inner collet cooperates with the truncated surface of the head of said bone screw, and said polyaxial movement being mobilized by release of the insert connected to said polyaxial inner collet wherein said insert locates at the truncated surface of the head of the selected bone screw; and
activating the selected inner collet by movement of an inner collet actuator arranged to engage the seat whereby activation of said selected inner collet effects its clamping about the common-shaped head of the selected bone screw.

\* \* \* \* \*